United States Patent [19]

Thomson

[11] 4,332,246
[45] Jun. 1, 1982

[54] POSITIVE DISPLACEMENT INTRAVENOUS INFUSION PUMP DEVICE AND METHOD

[75] Inventor: Thomas H. Thomson, Boulder, Colo.

[73] Assignee: Staodynamics, Inc., Longmont, Colo.

[21] Appl. No.: 164,105

[22] Filed: Jun. 30, 1980

[51] Int. Cl.³ .............................................. A61M 5/14
[52] U.S. Cl. ........................ 128/214 F; 128/DIG. 12
[58] Field of Search .......... 128/214 R, 214 D, 214 F, 128/DIG. 12, 218 A, DIG. 1

[56] References Cited

U.S. PATENT DOCUMENTS

| | | | |
|---|---|---|---|
| 3,054,401 | 9/1962 | Gewecke | 128/214 F |
| 3,228,395 | 1/1966 | Gewecke | 128/214 F |
| 4,090,514 | 5/1978 | Hinck et al. | 128/214 F |
| 4,270,533 | 6/1981 | Andres | 128/214 F |

Primary Examiner—John D. Yasko
Attorney, Agent, or Firm—O'Rourke & Harris

[57] ABSTRACT

A positive displacement intravenous infusion pump device and method are disclosed to precisely meter intravenous fluid to a patient. Intravenous fluid to be injected into the vein of a patient is placed in a closed rigid fluid container, and a variable (but fixed for each administration) quantity of incompressible material, stored in a separate receptacle, is introduced into the fluid container to cause displacement of fluid from the container to thereby inject the fluid into the vein of the patient. Introduction of incompressible material is controlled so that the intravenous fluid is injected in a controlled manner into the vein of the patient.

25 Claims, 3 Drawing Figures

POSITIVE DISPLACEMENT INTRAVENOUS INFUSION PUMP DEVICE AND METHOD

FIELD OF THE INVENTION

This invention relates to an intravenous infusion pump device and method and, more particularly, relates to a positive displacement intravenous infusion pump device and method.

BACKGROUND OF THE INVENTION

It is oftentimes necessary to inject a fluid into the body of a patient. For many years, such materials were fed to a patient only by the force of gravity which necessitated placing the container, containing the liquid for delivery to the patient, at a considerable elevation above the patient.

Such devices were not entirely satisfactory in view of the height requirement and difficulty in accurately regulating material flow. Regulation could only be secured by a hand-set tube clasp, and control was secured by counting the drops of fluid in a predetermined time, and then periodically checking by a nurse to determine that the desired rate of delivery was being maintained, because venous dilation changes cause variation in the resistance of flow of I.V. fluids into the body which modifies delivery rate. Gravity flow made it very difficult to maintain a regulated flow over a prolonged period of time.

In recent years, there has been considerable interest in intravenous delivery pumps for the infusion of saline solutions, and the like, to a patient, and there has been a trend toward developing a positive acting pump which could be accurate in its delivery of intravenous fluid medium to the patient, could be readily adjusted, and would be positive in its operation without requiring the placing of the bottle at some distance above the patient. Most pumps heretofore suggested, however, have been rather expensive and, hence, could not be used once and then discarded. Such pumps were difficult to disassemble, sterilize, and reassemble so that sterilization and maintenance of sterile conditions proved to be difficult.

In addition, known pumping devices draw from the intravenous containers and require air to be drawn into the intravenous fluid system to replace the volume of fluid displaced into the body, which can cause either contamination of the fluid from materials and organisms carried in the air or actual pumping of air into the patient's venous system (air embolism), if the pump is not shut off when the intravenous fluid container becomes empty.

The existing methods of allowing air to displace the fluid drawn from the intravenous fluid container system also results in volume delivery highly susceptible to pressure variation, causing variations in volumetric delivery. The extremes in volumetric delivery caused by pressure variation are unwanted and can cause repeated withdrawal and reinjection of the patient's blood or an overly-rapid delivery of fluid to the patient. These extreme cases can cause, respectively, damage to the patient's blood or toxicity from an excessive volume of some intravenous fluids.

Further, pumps of this nature can, under certain circumstances, be installed so that the action is reversed, thereby pumping blood from the patient until (and if) the fault is detected and corrected. Since known pumps operate with an open system, they will continue to pump air or fluid thereby causing either air embolism or draining the patient's blood supply, if not turned off at the appropriate time. Known pumps depend upon sensing means to detect failure modes of the pump, such as pumping air and blockage of the needle site (pressure build-up), and do not preclude the problems because of their inherent design. Such sensing means have been known to fail from time to time.

Prior art devices have heretofore been suggested for controlled liquid dispensing of a fluid in an intravenous solution (see, for example, U.S. Pat. No. 3,967,620), and devices have heretofore been suggested and/or utilized for dispensing of liquids through use of containers having compartments therein with the compartments containing the fluid being collapsed to cause fluid to be discharged therefrom (see, for example, U.S. Pat. Nos. 3,838,794; 3,506,005; 3,731,681; 3,797,492; 3,894,538; 3,756,459; 3,938,539; 3,955,557; and 3,974,825). In addition devices have herefore been suggested and/or utilized for causing a fluid to be dispensed utilizing mechanical means and/or vacuum means (see, for example, U.S. Pat. Nos. 3,884,228 and 3,965,946).

SUMMARY OF THE INVENTION

This invention provides a positive displacement intravenous infusion pump device and method which includes introducing incompressible material into a rigid container of intravenous fluid to thereby displace the fluid from the container and inject the same into the vein of a patient in a predetermined manner.

It is therefore an object of this invention to provide a positive displacement intravenous pump device and method.

It is another object of this invention to provide a positive displacement intravenous pump device and method wherein an incompressible fluid is introduced into a container to displace intravenous fluid therefrom.

It is still another object of this invention to provide a positive displacement intravenous pump device and method for accurately metering fluid to a patient both as to quantity and rate.

It is still another object of this invention to provide a positive displacement intravenous pump device and method wherein the rate of delivery is easily adjustable as needed or desired.

It is yet another object of this invention to provide an improved displacement intravenous pump device and method which inherently protects the patient from air embolism, backlash, contamination, unwanted removal of large quantities of blood, and yet provides a simple means of detecting infiltration.

It is yet another object of this invention to provide a positive displacement intravenous pump device and method that is simple and is inexpensive yet reliable in operation.

With these and other objects in view, which will become apparent to one skilled in the art as the discription proceeds, this invention resides in the novel construction, combination, arrangement of parts, and method substantially as hereinafter described, and more particularly defined by the appended claims, it being understood that such changes in the precise embodiments of the herein disclosed invention are meant to be included as come within the scope of the claims.

BRIEF DESCRIPTION OF THE DRAWINGS

The accompanying drawings illustrate complete embodiments of the invention according to the best modes so far devised for the practical application of the principles thereof, and in which.

DESCRIPTION OF THE INVENTION

Intravenous feeding fluids are commonly available from their manufacturers in one of two distinctly different storage and dispensing packages. One group of these packages is rigid bottles made of substances such as glass or plastic, while the second group of packages consists of containers made of soft and collapsible material, such as flexible plastic film in bag form.

Pump device 7 achieves beneficial results through isolation of the intravenous system from air, incompressibility of the system, and finite delivery capability, all of which are achieved by positive displacement of intravenous fluid by incompressible substances as disclosed in this invention.

Figure 1:
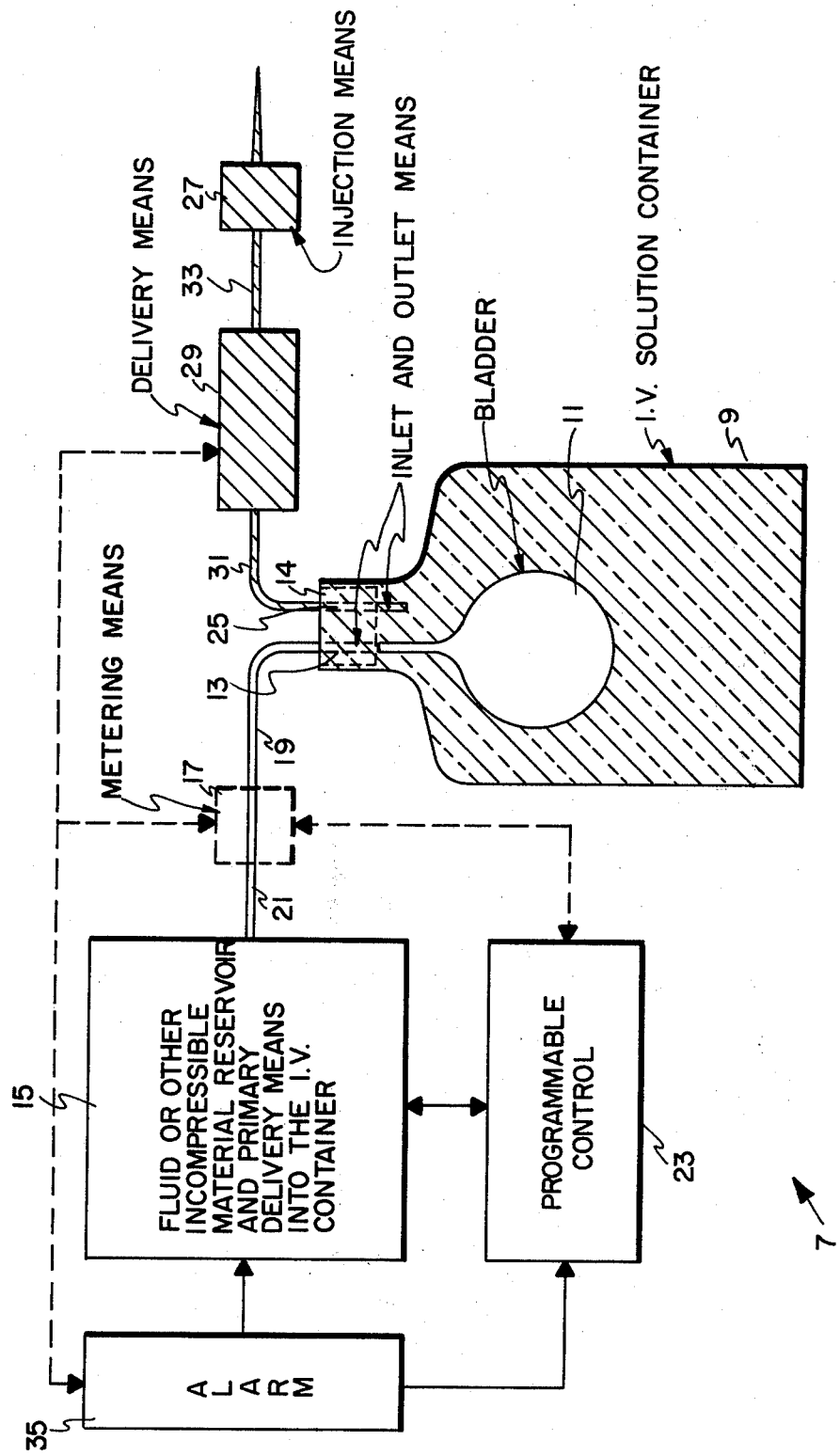
FIG. 1 is a combined block and schematic diagram for one embodiment of the pump of this invention.

As shown in FIG. 1, pump device 7 includes a rigid fluid container 9 (normally provided by the intravenous fluid supplier) which contains the intravenous fluid material. As can be appreciated, the quantity and specific intraveous fluid and the quantity of the incompressible material required to replace it are selected as necessary for the particular intravenous feeding needed by the patient.

A bladder, or other expandable means, 11 is placed in the container 9 and an inlet 13 (through stopper 14) provides an opening to bladder 11. Inlet 13 is connected to incompressible material storage receptacle 15 through an alternate metering device 17 and conduits 19 and 21. A programable control 23 controls operation of metering device 17 and hence controls introduction of incompressible material into bladder 11 within container 9. The incompressible material can be, for example, a fluid, such as water, and can also be a solid, and the programmable control can be any conventional device suitable for controlling opening and closing of a valve (including partial opening and closing) and could be, a metering device, such as for example, a mechanical drive with a cam and cam follower or an electronic programmer. In addition, the programmable control 23 may be of any means, mechanical or electronic, and may control either the metering means 17 or the mechanical primary delivery means 15 rate, or both.

Outlet 25 provides, through stopper 14, a discharge opening communicating with the interior of container 9. Outlet 25 is connected with an injection means 27 such as a needle, for example, for passage of fluid thereto, through the usual tubing, drip chambers, medication injection sites, etc., which constitute the delivery control system 29 and conduits 31 and 33. Delivery control system 29 can be utilized to sense the flow of fluid to the patient and can be connected with an alarm 35 (as can metering means 17) to indicate if the flow is either above or below a predetermined minimum such as, for example, if the flow essentially stops indicating a malfunction of the device.

While the mechanical rate of feeding speed of the primary delivery means 15 may be varied as needed to control the rate at which incompressible material is injected into bladder 11 within solution container 9, metering means 17 may also be used (as is indicated by the dashed lines of FIG. 1) as the primary method of controlling the rate at which incompressible material is injected into the I.V. container. When metering means 17 is so utilized, varying the mechanical rate of feeding speed of the primary delivery means 15 may be eliminated or may be utilized to act as a parallel system to that afforded by metering means 17 to thereby increase the certainty of achieving the desired rate of delivery of the incompressible material.

Conventional apparatus may be utilized for the IV container, conduits, delivery means, and injection means. In addition, bladder 11 could be eliminated from the system if the incompressible material used to displace the I.V. solution were of such a nature, liquid or solid, that it is not miscable with the I.V. solution and could not enter outlet 25 and be conducted through delivery system 29 and eventually into the patient.

Figure 2:
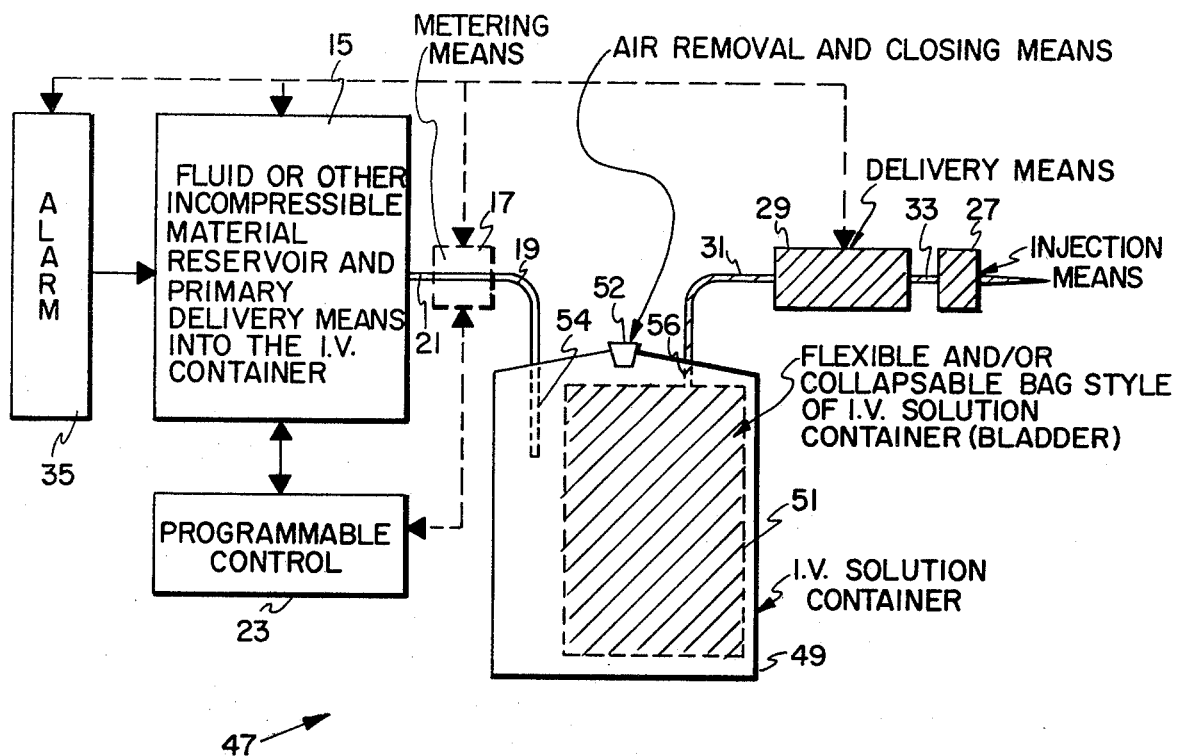
FIG. 2 is a combined block and schematic diagram of an alternate embodiment of the pump of this invention.

A second embodiment 47 of the invention is shown in FIG. 2. As shown, container 49 has bag 51 therein, which bag is of the flexible or collapsible bag style of I.V. solution containers, and the remaining volume of container 49 is filled with incompressible material, then sealed, as by stopper 52, to thereby produce a positive displacement system (through use of injection of incompressible material though inlet 54 and discharge of I.V. solution from the bladder 51 through outlet 56) which otherwise operates exactly as does the device as shown in FIG. 1. Thus, the distinction between the devices, as shown in FIGS. 1 and 2, and the methods of operation is that one uses an inflatable bladder or non-miscable, incompressible material to displace the I.V. solution (FIG. 1) while the other causes displacement of I.V. solution from a bladder (FIG. 2).

Figure 3:
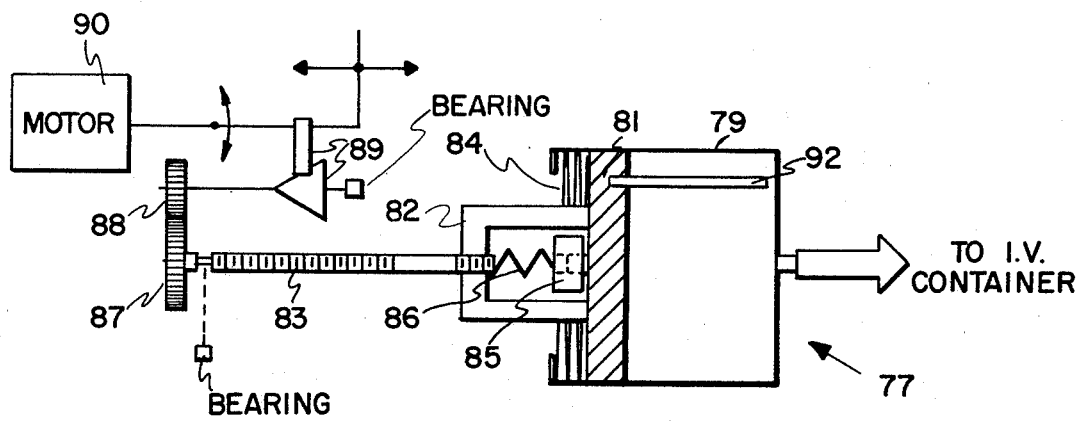
FIG. 3 is a combined, simplified block and schematic diagram of a primary delivery means of displacement which might be utilized in this invention.

A simplified pump 77, felt to be useful in this invention, is shown in FIG. 3. As shown, cylinder 79 is filled with incompressible material. Piston 81 is moved forward by a rotating screw 83, turning in the threaded base 82 of piston 81. The rotating screw 83 has its threads periodically interrupted, allowing spring 84 to cause piston 81 to retract a distance sufficient to verify that infiltration is not occurring. Nut 85 is spaced from the threaded base of piston 81 sufficiently to ensure that spring 86 creates sufficient tension to eventually offset the pull of spring 84. Spring 84 is overcome sufficiently to allow screw 83 to re-engage the threaded base of piston 81 and force the continuation of the forward motion of piston 81. Screw 83 is driven by gears 87 and 88 with gear 88 being rotatively driven by conventional friction cone drive 89, thereby providing continuous variability in the speed of piston 81 forward motion. As shown, friction cone drive 89 is driven by a motor 90. The exact quantity of incompressible material present or displaced can be read directly by the position of the piston 81 viewed in relationship to a graticule 92 inscribed on a clear portion of cylinder 79.

In operation, the incompressible material is introduced into the container having the intravenous fluid therein under control so that the fluid in the container is precisely metered from the container into the vein of the patient. The fluid can be metered in at a constant rate, or differing rates, if desired, and is carefully controlled both as to quantity and rate. In addition, by periodically withdrawing incompressible material from the container, this causes a small amount of blood to be drawn from the vein into the clear tubing above the needle site to thus provide assurance of continued proper placement of the needle in the vein. The presence of blood may be ascertained visually and/or electronically.

This invention thus provides a precise metering pump device and method specifically designed to displace fluids from intravenous fluid containers (including currently available containers) through the use of incompressible materials. The device and method departs from the presently known devices and methods which include pumping fluids from the fluid container.

In the device and method of this invention, an incompressible substance is pumped into the fluid container to thereby displace the intravenous fluid therein, to achieve the following advantages:

1. Air is completely eliminated from the system; therefore, the danger of air embolism is non-existant and contamination from air filtered through the intravenous fluids to replace fluids drawn from the container is eliminated;
2. Pump backlash is eliminated since the system is incompressible and fluids can not reenter the intravenous system because of uncontrolled pressure variations and/or pump malfunction;
3. Because the system is incompressible, the quantity of fluids displaced is independent of back pressure introduced by changes in the patient's degree of vasodilation (widening of the lumen blood vessels);
4. Volumetric displacement produces pressures in the system only sufficient to cause the transfer of fluid volume displaced;
5. By reversing the pumping action, fluids are drawn on an appropriate regular basis from the patient and if the fluid withdrawn is not blood, this indicates that the needle used to induce the intravenous fluid into the patient has moved from the vein and is allowing the fluid to infiltrate into tissue, or is disconnected from the patient.
6. Because the incompressible fluid fills the I.V. solution container and is prevented from entering the delivery means, very precise control is maintained over the total volume of substances delivered;
7. The nature of the actual pumping mechanism is such that very simplified apparatus may be used (a plausible example is shown in FIG. 3), thereby reducing costs and increasing reliability of the device and method herein disclosed;
8. Because the incompressible material and the I.V. solution are separated in the I.V. solution container and because the I.V. solution container is fixed in volume, any malfunction of the device which would cause the pump to operate in reverse would self-limit the amount of blood drawn from the patient; and
9. For complete displacement of virtually all of the IV fluid solution from the IV solution container, the amount of incompressible material is made to equal the amount of fluid in the IV solution container.

In view of the foregoing, it should be appreciated that the device and method of this invention provides a novel positive displacement intravenous infusion pump device and method.

What is claimed is:

1. In a positive displacement infusion device for injecting a solution from a container through a discharge means into a patient, delivery means for introducing an incompressible material into said container to cause said solution stored therein to be displaced from said container through said discharge means in an amount proportional to the amount of incompressible material introduced into said container, said delivery means including control means for controlling introduction of said incompressible material into said container whereby solution is discharged from said container through said discharge means in a predetermined manner.

2. The device of claim 1 wherein said delivery means includes storage means for storing said incompressible material, inlet means communicating into the interior of said container, and conveying means for conveying incompressible material from said storage means to said inlet means.

3. The device of claim 2 wherein said control means includes means for controlling withdrawal of said incompressible material from said storage means.

4. The device of claim 3 wherein said control means includes means for controlling withdrawal of incompressible material at an adjustable rate from said storage means.

5. The device of claim 4 wherein said withdrawal controlling means includes a programmable control for controlling release of incompressible material from said storage means.

6. The device of claim 5 wherein said control means includes metering means connected between said storage means and said container, said metering means being controlled by said programmable control to control release of said incompressible material from said storage means to said container.

7. The device of claim 6 wherein said control means includes alarm means connected with said metering means, storage means and programmable control.

8. The device of claim 4 wherein said withdrawal controlling means includes drive means for controlling release of incompressible material from said storage means.

9. The device of claim 8 wherein said container includes a cylinder having a volume determining piston therein, and wherein said drive motor is mechanically linked to position said piston.

10. The device of claim 1 wherein said delivery means includes means for enabling periodic withdrawal of incompressible material from said container to ensure proper operation of said device.

11. A positive displacement intravenous infusion pump comprising:
a closed container having a fluid therein to be intravenously fed to a patient;
an inlet and an outlet leding to the interior of said container;
injecting means for injecting said fluid into the vein of a patient;
means connecting said outlet with said injection means for conveying fluid from said container through said outlet to said injection means;
storage means for storing incompressible material;
means connecting said storage means with said inlet for conveying incompressible material from said storage means to said container through said inlet; and
control means for controlling delivery of said incompressible material to said container whereby fluid in said container is accurately injected into the vein of a patient having said injection means inserted therein.

12. The pump of claim 11 wherein said container has a bladder therein communicating with said inlet whereby incompressible material introduced into said container is confined within said bladder.

13. The pump of claim 11 wherein said container has a bladder therein communicating with said outlet, and wherein said inlet permits introduction of incompressible material into said container outside of said bladder.

14. The pump of claim 11 wherein said control means includes material metering means connected to control passage of incompressible material through said means connecting said storage means with said inlet, and a programmable control for controlling operation of said material metering means.

15. The pump of claim 14 wherein said means connecting said outlet with said injecting means includes fluid delivery means, and wherein said control means includes alarm means connected with said fluid delivery means, material metering means, storage means, and programmable control.

16. The pump of claim 11 wherein said storage means is a cylinder having a piston therein, and wherein said control means includes actuating means connected with said piston, said actuating means including a screw rotatively driven by a motor through a mechanical linkage that includes a friction cone drive and meshed gears.

17. The pump of claim 11 wherein said control means includes means for enabling periodic withdrawal of incompressible material from said container to ensure proper operation of said pump.

18. A method for positively displacing a solution from a container into a patient, said method comprising:
    introducing an incompressible material into said container to cause said solution in said container to be displaced therefrom and injected into a patient; and
    controlling introduction of said incompressible material into said container whereby said fluid is accurately injected into said patient in a predetermined manner.

19. The method of claim 18 wherein said method includes maintaining said container air free.

20. The method of claim 18 wherein said incompressible material is introduced into a bladder within said container and thus maintained free of contact with said fluid in said container.

21. The method of claim 18 wherein said solution is within a bladder within said container, and wherein said incompressible material is introduced into said container outside said bladder and thus maintained free of contact with said solution within said bladder.

22. The method of claim 18 wherein control of introduction of incompressible material into said container includes periodic withdrawal of incompressible material from said container to ensure proper operation of intravenous feeding.

23. A method for positively displacing fluid for intravenous feeding of a patient, said method comprising:
    providing a closed container having a predetermined amount of intravenous fluid therein;
    connecting said container with a discharge system for discharging fluid from said container into the vein of a patient;
    providing a storage receptacle;
    placing an incompressible material in said storage receptacle;
    delivering said incompressible material from said storage receptacle to said container to cause displacement of fluid from said container; and
    controlling delivery of said incompressible material from said receptacle to said container whereby said fluid is precisely metered into the vein of said patient.

24. The method of claim 23 wherein said method includes sensing delivery of said fluid to said patient and sounding an alarm if not within predetermined limits.

25. The method of claim 23 wherein said method includes periodically withdrawing incompressible material from said container to cause withdrawal of a small amount of blood from said vein to assure proper operation of said intravenous feeding.

* * * * *

UNITED STATES PATENT AND TRADEMARK OFFICE
CERTIFICATE OF CORRECTION

PATENT NO. : 4,332,246
DATED : June 1, 1982
INVENTOR(S) : Thomas H. Thomson

It is certified that error appears in the above—identified patent and that said Letters Patent is hereby corrected as shown below:

Column 6, line 50, after "closed" insert --rigid--.

Column 6, line 52, delete "leding" and insert --leading--.

Column 8, line 19, after "closed" insert --rigid--.

Signed and Sealed this

Twenty-first Day of September 1982

[SEAL]

Attest:

Attesting Officer

GERALD J. MOSSINGHOFF

Commissioner of Patents and Trademarks